(12) United States Patent
Zinser

(10) Patent No.: US 7,971,999 B2
(45) Date of Patent: Jul. 5, 2011

(54) METHOD AND APPARATUS FOR RETINAL DIAGNOSIS

(75) Inventor: Gerhard Zinser, Speyer (DE)

(73) Assignee: Heidelberg Engineering GmbH, Heidelberg (DE)

( * ) Notice: Subject to any disclaimer, the term of this patent is extended or adjusted under 35 U.S.C. 154(b) by 277 days.

(21) Appl. No.: 12/312,237

(22) PCT Filed: Nov. 2, 2007

(86) PCT No.: PCT/EP2007/009526
§ 371 (c)(1),
(2), (4) Date: Apr. 30, 2009

(87) PCT Pub. No.: WO2008/052793
PCT Pub. Date: May 8, 2008

(65) Prior Publication Data
US 2010/0053553 A1      Mar. 4, 2010

(30) Foreign Application Priority Data
Nov. 2, 2006   (DE) .......................... 10 2006 052 149

(51) Int. Cl.
*A61B 3/00* (2006.01)
*A61B 3/14* (2006.01)

(52) U.S. Cl. .................. 351/246; 351/206; 351/209

(58) Field of Classification Search .................. 351/200, 351/205, 206, 209, 246
See application file for complete search history.

(56) References Cited

U.S. PATENT DOCUMENTS
2004/0036838 A1   2/2004   Podoleanu et al.
2005/0261595 A1   11/2005  Michelson FOREIGN PATENT DOCUMENTS
EP   1 487 322        12/2004
EP   1 836 952        9/2007
WO   WO-2006/058735   6/2006
WO   WO-2007/061769   5/2007

OTHER PUBLICATIONS

Yannuzzi L. A. et al., "Ophthalmic Fundus Imaging: Today and Beyond", American Journal of Ophthalmology, Ophthalmic Publ. Chicago, IL., US, vol. 13y, No. 3, Mar. 2004, pp. 511-524.

*Primary Examiner* — Jack Dinh
(74) *Attorney, Agent, or Firm* — Jordan and Hamburg LLP

(57) ABSTRACT

The invention relates to a method and an appliance for examination of the retina, with two-dimensional images of the retina being produced. The invention is based on the object of designing the method and the apparatus so as to allow comprehensive examination and diagnosis of the eye retina in a simple manner. The invention proposes that second data items and two-dimensional depth slice images be produced from the retina, and that the position of these second data items be known in the recorded two-dimensional image of the retina, and/or be predetermined on the basis of the two-dimensional image.

20 Claims, 2 Drawing Sheets

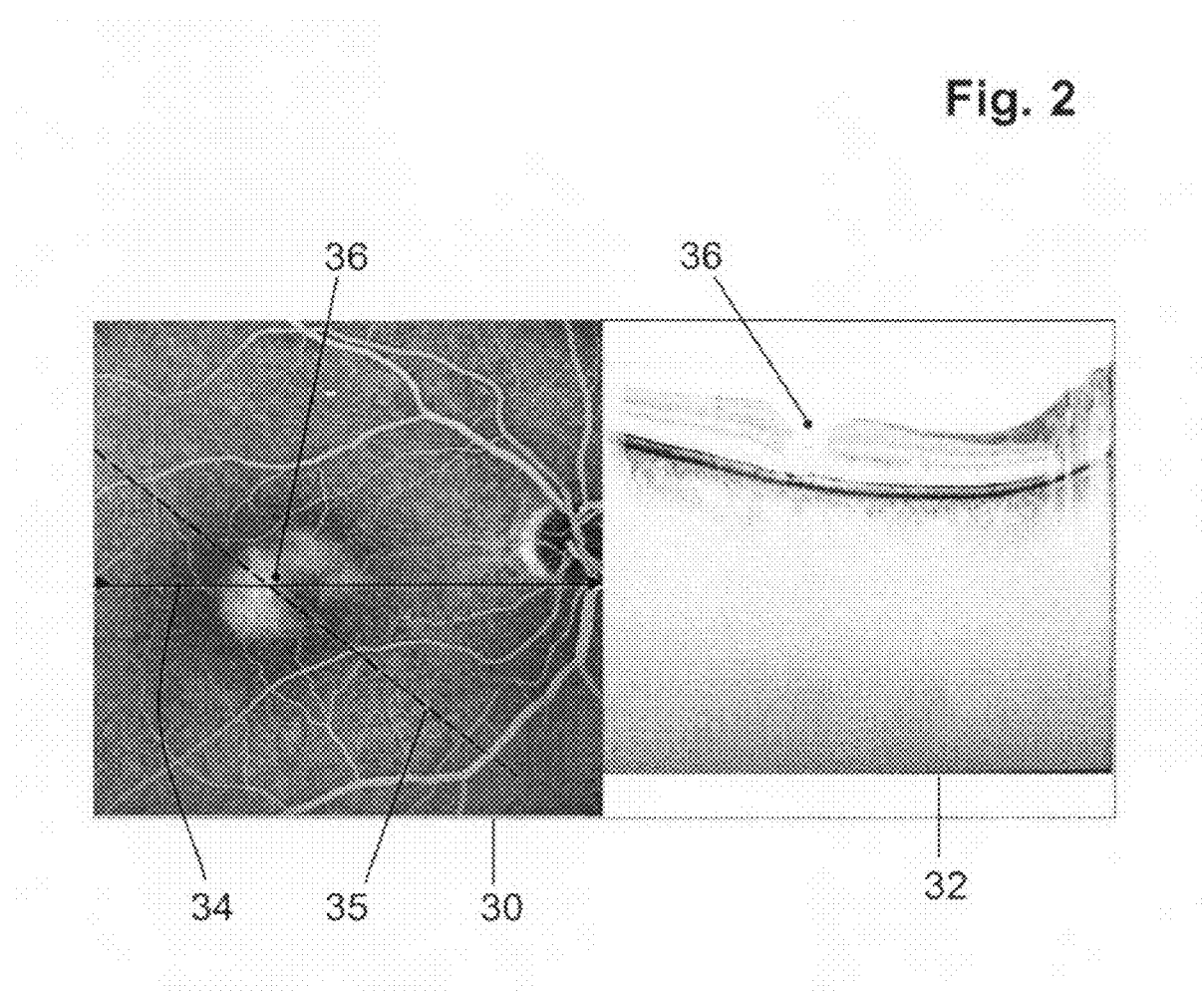

METHOD AND APPARATUS FOR RETINAL DIAGNOSIS

BACKGROUND OF THE INVENTION

The invention relates to a method for retinal diagnosis. The invention furthermore relates to an apparatus for performing the method.

Such a method is known from EP 1 487 322 B1, which is for examining cavities of the retina in an eye and determining the cavity wall thickness. Laser scanning is used to determine the external diameter and the internal diameter of the cavity, and then the wall thickness of the cavity is determined from the data thus obtained. The external cavity diameter is determined from the data of a reflectivity image, and the internal diameter is determined from the data of a laser Doppler image according to the diameter of the blood column moved. Comprehensive examination and diagnostics of the retina is not possible without anything further. The laser scanning technology is used for producing reflectivity images, angiography images, and auto-fluorescent images of the retina. A laser beam with a specific wavelength scans the retina point by point in a two-dimensional field, and the result is continuous live images or reference images, 10 to 50 images per second being typical. The angiography, in particular in the form of fluorescein angiography (FA) and indocyanine green angiography (ICGA), is an important diagnostic procedure in which essentially two-dimensional images of the retina surface, and where necessary, deeper layers of the retina, are produced by illuminating and scanning in a point-by-point manner. Furthermore, such planar images can be produced using flat illumination and acquisition by a suitable imaging sensor such as for instance a CCD (charge coupled device) camera or a fundus camera. Moreover, spectral-domain optical coherence tomography (OCT) is used for retinal diagnosis; it provides two-dimensional slice images essentially perpendicular to the retinal surface, so-called B scans, that are combined linearly from A scans that go deep into the fundus. Two different apparatus are required for producing the aforesaid planar images and the depth slice images, and this results in significant complexity. In terms of the various known methods, examining and diagnosing the retina of the eye is very demanding for an examiner, but also for a patient, and in addition it is time consuming, sometimes requiring that examinations be performed successively using different apparatus.

Proceeding from this state of the art, the underlying object of the invention is to propose a method that makes possible, in a simple manner, a comprehensive examination and diagnosis of the retina of the eye. It should be possible to perform the method without a problem and in a functionally safe manner, and to provide reliable results with a low degree of complexity while rendering diagnosing easier for the examiner. The apparatus for performing the method should have a simple and/or functionally safe structure, should not be complex to operate, and should enable optimized and/or comprehensive retinal diagnosis.

SUMMARY OF THE INVENTION

The method and the apparatus proposed for performing the method in accordance with the invention make it possible to perform comprehensive examinations of the retina based on the production of planar images combined with depth slice images of the retina, a planar image and a depth slice image being displayed concurrently or successively or simultaneously by means of one or a plurality of display units, such as monitors or displays. In a preferred manner, an examiner can select and/or specify any desired position and/or orientation for the depth slice image in the planar image, taking into account an area of interest depicted therein, in particular, a visible pathology. The method and apparatus are used in a preferred manner for comprehensive retinal diagnosis.

The planar images are preferably two-dimensional images of at least sections of the retina surface and/or planes of the retina that are at least nearly parallel thereto. The planar images are preferably produced using angiography, but in the framework of the invention, reflectivity images of any desired wavelength or auto-fluorescence images or images acquired using flat illumination or by means of a camera, like a CCD sensor, may also be used and displayed instead. The depth slice images of the retina are preferably produced using optical coherence tomography (OCT), but in the framework of the invention, other methods, such as ultrasound, may also be used.

The apparatus in accordance with the invention is characterized by the integration and combination of two independent system components, by means of which components, the planar images can be produced and the depth slice images can be produced. Thus, the one system component preferably contains a laser scanning system having different laser sources for recording reflectivity and angiography images, two oscillating mirrors with which the focused laser beam sequentially scans a two-dimensional area of the retina, and a detector that measures the quantity of light reflected or emitted at each point. The other system component preferably contains a spectral domain OCT system having a broadband light source, such as, for instance, a super-luminescent diode, two additional scanning mirrors for scanning the retina, and a spectrometer. However, other OCT techniques may also be used. The beam paths for the two system components are matched to one another at a location that is disposed between the eye being examined and the scanning mirrors, and specifically, in particular, using an optical unit and/or optical splitting and imaging unit. Using the apparatus, there is a simultaneous and/or concurrent recording of one of the planar images, and/or successive recording of one of the planar images in pre-specifiable, preferably brief, time intervals, which recording is also called a live reference image, with one of the depth slice images, which is also called an OCT scan or OCT live image. A reference image is preferably either an angiography image or a reflectivity image, or an auto-fluorescent image. The location on the retina at which the depth slice image is produced, in particular the OCT live image, and the orientation of the depth slice image, can be freely selected and/or pre-specified by the user, for instance by clicking the mouse in the reference image.

Furthermore, in accordance with the method and/or with the apparatus, the eye movement of a patient is measured using the resultant movements of the structures visible in the reference image. The depth slice image, in particular the OCT live image, is stabilized such that the eye movements measured by means of the reference image are fed back to the optical unit, e.g., the scanning mirrors of the OCT system component and/or such that the location in the retina at which the OCT live image is obtained follows the eye movements, and thus a stable image is always recorded and/or produced at the same location. Moreover, a plurality of successive OCT live images that have been stabilized, as explained in the foregoing, can be averaged in order to increase the signal-to-noise ratio and thus increase the quality of the OCT live images. Furthermore, the averaged images are preferably displayed, for instance, as a sliding average instead of the normal depth slice image, in particular, instead of the OCT live image.

In accordance with one preferred embodiment of the invention, during the stabilization, a plurality of depth slice images and/or OCT images that run parallel to one another, but that are slightly offset from one another, are automatically recorded. Each of these images can be a temporal average of a plurality of successive images at the same location, and the quantity of images thus averaged jointly forms a three-dimensional depth slice image and/or a three-dimensional OCT image.

In accordance with one special refinement, the exact position and orientation in the reference image and the reference image itself of a depth slice image and/or OCT image recorded during an examination are stored, in particular, in a suitable memory. Moreover, the information stored in this manner is used to automatically adjust the deflection unit and/or the scanning unit, in particular the scanning mirrors of the OCT system component, during a subsequent or follow-up examination, such that the depth slice image and/or the OCT image from the follow-up examination is recorded at exactly the same location as in the previous examination. Thus, it is possible in a preferred manner to directly compare the aforesaid images directly for changes in the retina.

Using the method, and likewise with the apparatus, according to the invention, first data items and first two-dimensional and/or planar images of at least areas of the retina are produced, and furthermore second data items and two-dimensional depth slice images are produced from the retina, the position and/or orientation of the depth slice image(s) with respect to the retina surface being pre-specified. The location or area of interest, especially the area of pathology that is visible in the two-dimensional image or planar image, at which location the depth slice image is produced, and furthermore its orientation, are thus selected and/or pre-specified using the planar image or reference image. It is furthermore of great significance that the first planar image and the depth slice image are displayed concurrently or simultaneously, or even in pre-specifiable or pre-specified temporal, preferably brief, intervals. The depth slice image is stabilized by feedback, in particular to the scanning or deflection unit, such that the location or the area of the retina at which the depth slice image is obtained follows and/or tracks the eye movements. Moreover, in a preferred manner, a plurality of successive, in particular, stabilized, depth slice images are averaged, the averaged depth slice image(s) preferably furthermore being displayed in particular as a sliding average. Moreover, during the stabilization, a plurality of depth slice images that run largely parallel to one another, and that are offset in pre-specified small intervals, are automatically recorded or produced. Preferably, a three-dimensional image is produced from a plurality of successive, preferably stabilized, slice images. Furthermore, the position and/or orientation of the preferably stabilized depth slice image and/or of the three-dimensional depth slice image and furthermore preferably also the associated planar or reference image are stored.

The method and the apparatus suggested for performing the method according to the invention include the combination of producing planar images of the retina and producing second data items and two-dimensional depth slice images from the retina, the position of the second data items being known and/or stored in the recorded two-dimensional planar image of the retina. The position and/or orientation of one or a plurality of depth slice images is controlled and/or actively managed and/or pre-specified using the planar image, and thus the position and/or orientation of one or a plurality of depth slice images is pre-specified and/or actively controlled using a two-dimensional image or planar image that was recorded earlier. Furthermore, the position and/or orientation of one or a plurality of depth slice images is preferably pre-specified using a first recorded planar image, and actively controlled by updating the planar image. Preferably, the movement of the updated planar image is determined relative to the first recorded planar image, and the position of the recording or production of one or a plurality of depth slice images is managed at the pre-specified sites or locations of the retina. It is particularly significant that the first planar image or the updated planar image and the depth slice image are displayed concurrently and/or simultaneously or in pre-specifiable temporal intervals by means of one or a plurality of display units. The depth slice image is stabilized by feedback such that the location of the retina at which the planar slice image is obtained tracks the eye movements. Moreover, it has proved useful when a plurality of successive stabilized depth slice images are averaged and/or the averaged planar slice image(s) is/are displayed, in particular, as a sliding average. In a preferred manner, during the stabilization a plurality of depth slice images that run parallel to one another or according to any desired and/or pre-specifiable pattern and that are offset in pre-specifiable small intervals are automatically recorded. In a preferred manner, a three-dimensional depth slice image is produced from these depth slice images and/or from a plurality of successive depth slice images.

Moreover, the position of the depth slice image in the reference image and the reference image itself are stored, and the depth slice image is recorded or produced in a follow-up examination at exactly the same location and/or with the same orientation as in a previous examination, and is also stored for further examinations.

The two-dimensional planar image is usefully produced using reflected or re-emitted light in one or a plurality of selected wavelength ranges or, for recording the planar image, the retina is illuminated with light from a selected wavelength range or a plurality of selected wavelength ranges. Furthermore, for recording or producing the two-dimensional planar image the illumination can be by means of a point that scans the pre-specified area of the retina, or the illumination can be performed using a line that is conducted over the pre-specified area of the retina. Detection can be performed by means of a point detector or by means of a line camera or by means of a planar camera. The OCT slice images are advantageously recorded using a Fourier domain OCT method or a time domain OCT method. Preferably the two-dimensional planar image is an angiography image. In one special embodiment of the invention, a first angiography image and a second two-dimensional planar image, for example, a reflectivity image, of the retina are recorded concurrently or concurrently at a very brief temporal interval, the recording of the depth slice images being controlled and managed by updating the second two-dimensional planar image of the retina. If there is a follow-up examination, this second planar image can then be used instead of the first planar image for controlling, managing, and stabilizing the depth slice images. In accordance with the invention, producing the planar images as angiography images in combination with the OCT slice images and their simultaneous display is particularly significant.

The invention is described in greater detail in the following using a special exemplary embodiment with reference to the following drawings, but this shall not constitute a restriction of the contemplated scope.

BRIEF DESCRIPTION OF THE DRAWINGS

FIG. 2 are the images displayed adjacent to one another in a display element; specifically the planar image as an angiography image on the left and the depth slice image as an OCT live B scan image on the right.

DETAILED DESCRIPTION OF THE INVENTION

Figure 1:
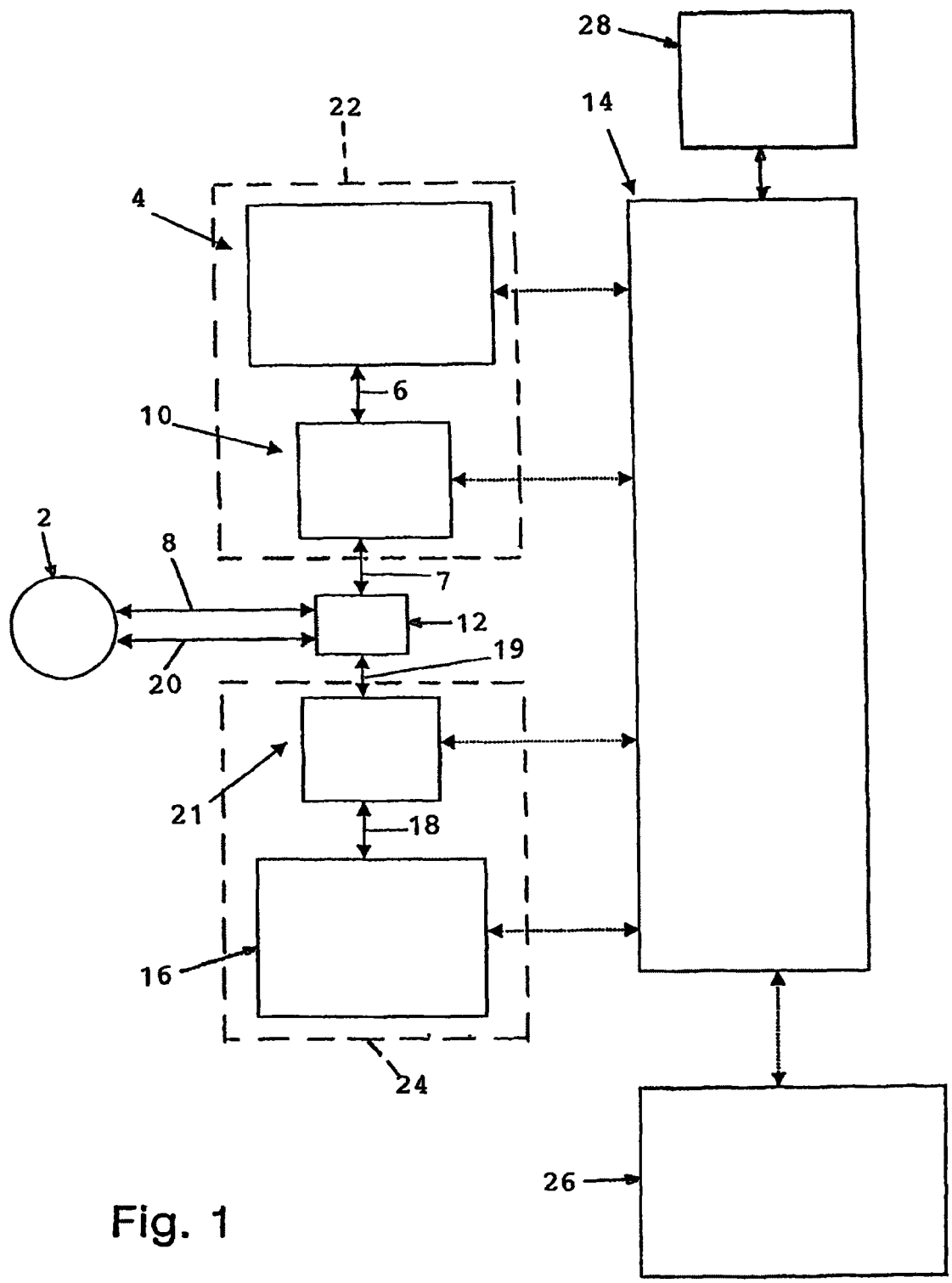
FIG. 1 is a circuit diagram depicting an embodiment of the invention.

In accordance with FIG. 1, for comprehensive examination of the retina of the schematically depicted eye 2, the apparatus contains an image acquisition unit 4 for first two-dimensional images or planar images of the retina. The image acquisition unit 4 contains an illumination unit and a measuring unit. As indicated by the arrows 6, 7, 8, the illumination unit illuminates the retina, specifically at a point, on a line, or on a plane. The light travels via a scanner control unit 10 and an optical unit 12 to the retina. In a known manner, the scanner control unit 10 contains scanning mirrors or the like and, like the image acquisition unit 4, is also controlled by a control and processing unit 14. A scanner 16 is provided for producing depth slice images of the retina. The light reflected and/or re-emitted by the retina travels according to the arrows 8, 7, 6 into the image acquisition unit 4, the measuring unit of which is the intensity of the light that is reflected overall from one point in the retina and/or re-emitted light or the intensity of the light reflected and/or re-emitted in a selected wavelength range. The measuring unit is embodied either as a point detector or line camera or planar camera.

The OCT scanning beam for the OCT image recording scans an area of the retina point-wise or line-wise, a depth profile, a so-called OCT A scan, being recorded at each point. As indicated by the arrows 18, 19, 20, the light travels from the scanner 16 via the OCT scanner control 20 and the optical unit 12 to the retina and back. The OCT scanner 16 and the OCT scanner control 21 are also controlled by means of the control and processing unit 14. Based on the control by the scanner control unit 10 and the OCT scanner control 21, the coordinates of the OCT recording and the unit 4 are known and can thus be coordinated relative to one another. In particular the OCT scanning beam can be controlled relative to the fixed positions and/or areas of interest. In a preferred manner, the OCT scanning beam can track any movements, in particular in the period between individual recordings by the image acquisition unit 4.

The image acquisition unit 4 and the scanner 10 form a first system component 22 and the OCT scanner 16 with the OCT scanner control 21 form a second system component 24, the beam paths of which are combined at one location and/or by means of the optical unit 12. The optical unit 12 is a shared part and imaging unit for the two system components 22, 24 and/or their beam paths. As can be seen, the optical unit 12 is inventively arranged in the beam paths between the eye 2 and the scanner control unit 10 for the planar images on the one hand and the scanner control 21 for the depth slice images, in particular the OCT scanner control, on the other hand. Attached to the control and processing unit 14, is another unit 26 for operation and evaluation, and it also advantageously contains a data base and/or memory and/or a CPU or other computer modules. Finally, attached to the control and processing unit 14 is a display unit 28, by means of which the planar image, in particular, the angiography image, and the OCT live B scan image are displayed.

FIG. 2 shows the two images displayed by means of the image display unit, specifically the angiography image 30, on the left and the OCT live B scan image 32 on the right. The location at which the depth slice image or OCT live B scan image is recorded is marked on the angiography image 30 by means of the line 34. The line 34 is placed through an area 36 and in the OCT live B scan image 32 on the right additional significant details of this area 36 of interest are displayed for the examiner so that they are easy to visualize and evaluate. The user or examiner can specify the position of the line 34 and/or its orientation in the planar image 30, and thus with respect to the retina, with no problem according to his experience and desires; another line 35, this line being broken, is added as an example with a different position and orientation, and a correspondingly changed depth slice image or OCT live B scan image can be displayed for the area of interest taken along line 34.

The invention claimed is:

1. A method for examining the retina, comprising:
producing and recording first data items and planar images of the retina by operating a first system component that includes a first scanner;
selecting and pre-specifying positions and the orientations of two-dimensional depth slice images on respective ones of said planar images;
further producing and recording second data items and the two-dimensional depth slice images of the retina by operating a second system component that includes a second scanner and a scanner control; and
stabilizing said depth slice images to said scanner of said second system component by utilizing feedback of eye movements measured by means of each of said planar images, such that respective locations of the retina at which the depth slice images are produced and recorded are obtained by tracking the eye movements.

2. A method according to claim 1, wherein a position and/or orientation of at least one of said depth slice images is controlled, actively managed and/or pre-specified using at least one of said planar images or at least one of the planar images previously recorded.

3. A method according to claim 2, wherein the position and orientation of said at least one of said depth slice images is pre-specified using a first recorded one of said planar images and is actively controlled by updating the planar images with an updated planar image, and/or the movement of the updated planar image is determined relative to the first recorded one of the planar images.

4. A method according to claim 3, wherein said first recorded one of said planar images or the updated planar image, and a corresponding one of said depth slice images, are displayed concurrently, simultaneously or in pre-specifiable time intervals by utilizing at least one display unit.

5. A method according to claim 1, further comprising determining an average for successive ones of said depth slice images to yield at least one averaged depth slice image.

6. A method according to claim 5, wherein said depth slice images are stabilized depth slice images and/or the at least one averaged depth slice image is displayed as a sliding average.

7. A method according to claim 1, wherein, during the stabilization, a plurality of depth slice images that run parallel to one another or that run according to a desired and/or pre-specified pattern and are offset from one another in pre-specified intervals, are automatically recorded.

8. A method according to claim 1, wherein a three-dimensional depth slice image is produced from a plurality of successive depth slice images.

9. A method according to claim 1, further comprising:
storing the positions of said depth slice images and said planar images;
recording a further depth slice image from a follow-up examination at exactly a same location and with a same orientation as in a previous examination; and
further storing a position of the further depth slice image.

10. A method according to claim 1, wherein said two-dimensional planar images are produced using re-emitted light in at least one selected wavelength area.

11. A method according to claim 1, wherein, for the recording or producing at least one of said planar images, the retina is illuminated with light from at least one selected wavelength range.

12. A method according to claim 1, wherein illumination for recording said planar images is provided in a point that scans an area of the retina or in a line that is conducted across the area of the retina.

13. A method according to claim 1, wherein said operating the first system component includes detecting performed by a point detector, a line camera or a planar camera.

14. A method according to claim 1, wherein said depth slice images are recorded according to a Fourier domain OCT method or according to a time domain OCT method.

15. A method according to claim 1, wherein at least one of said two-dimensional planar images is an angiography image.

16. A method according to claim 15, wherein:
a first angiography image and a second two-dimensional retina image and/or planar image are recorded concurrently or at very brief temporal intervals; and
in that the recording of the depth slice images is controlled and managed by updating the second planar image.

17. A method according to claim 15, wherein:
said at least one of said two-dimensional planar images includes a combination of planar angiography images; and
said depth slices are simultaneously produced and/or displayed.

18. A method, in particular according to claim 15, wherein said depth slice images include OCT depth slice images.

19. A device for examining a retina of an eye, comprising:
a first system component including an image acquisition unit and a scanner control unit for producing planar images; and
a second system component including a scanner and a scanner control for producing depth slice images, respective beam paths of said first and second system components being combined in a shared optical unit and output therefrom as combined beams, the combined beams being directable at the eye to be examined and being returned therefrom to said optical unit as combined return beams, said optical unit being structurally configured such that there is a corresponding division of said combined return beams to said first system component and said second system component.

20. An apparatus according to claim 19, further comprising:
a shared control and processing unit for said two system components;
an operation and evaluation unit being attached to said control and processing unit; and
a display unit for said planar images and for said depth slice images.

* * * * *